United States Patent

Omatsu et al.

Patent Number: 5,773,666
Date of Patent: Jun. 30, 1998

[54] HYDROFORMYLATION PROCESS

[75] Inventors: Toshihiro Omatsu, Hasaki-machi; Jin Tokuyasu; Masahiro Muranaka, both of Kamisu-machi; Takashi Onishi, Hasaki-machi, all of Japan

[73] Assignee: Kuraray Co., Ltd., Kurashiki, Japan

[21] Appl. No.: 836,880

[22] PCT Filed: Sep. 26, 1996

[86] PCT No.: PCT/JP96/02771

§ 371 Date: May 27, 1997

§ 102(e) Date: May 27, 1997

[87] PCT Pub. No.: WO97/11931

PCT Pub. Date: Apr. 3, 1997

[30] Foreign Application Priority Data

Sep. 26, 1995  [JP]  Japan ..................................... 7-271948

[51] Int. Cl.$^6$ .................................................. C07C 45/50
[52] U.S. Cl. ........................................... 568/454; 568/451
[58] Field of Search ..................................... 568/454, 451

[56] References Cited

U.S. PATENT DOCUMENTS 5,180,854  1/1993  Abatjoglou et al. .................... 568/454

FOREIGN PATENT DOCUMENTS 52-105590 A  9/1977  Japan .
58-208243 A  12/1983  Japan .
63-190844 A  8/1988  Japan .

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

Described is a process for hydroformylation of an olefinic compound, which comprises, carrying out the reaction in the presence of:

a) a rhodium compound, b) a tertiary organic phosphorus compound represented by the following formula (1):

$$P(X_1)(X_2)(X_3-SO_3M) \qquad (1)$$

wherein $X_1$ and $X_2$ each independently represents a monovalent hydrocarbon group having 1–15 carbon atoms and $X_3$ represents a divalent hydrocarbon group having 1–15 carbon atoms and M represents an alkali metal, and c) a polar organic compound; separating the rhodium compound, the tertiary organic phosphorus compound represented by the formula (1) and the polar organic compound from the resulting reaction mixture by extraction with water; subjecting the extracted water layer to removal of water and addition of at least one acidic substance selected from sulfonic acids to prepare a concentrate containing the rhodium compound, the tertiary organic phosphorus compound represented by the formula (1) and the polar organic compound; and recycling the resulting concentrate to a reactor for reuse.

6 Claims, No Drawings

HYDROFORMYLATION PROCESS

This is a 371 of PCT/JP96/02771, filed Sep. 26, 1995.

TECHNICAL FIELD

This invention relates to a process for the hydroformylation of an olefinic compound. A hydroformylated product obtained by the present invention is useful as a starting material for fine chemicals such as pharmaceuticals and agricultural chemicals, alcohols for a plasticizer, or starting materials such as diol, dicarboxylic acid, and diamine for the synthesis of a polymer compound.

BACKGROUND ART

A process for preparing an aldehyde by the reaction of an olefinic compound with hydrogen and carbon monoxide using a rhodium compound as a catalyst is called hydroformylation reaction or oxo reaction and it is an industrially useful synthetic process. The rhodium compound is, however, markedly expensive. So, in order to carry out the hydroformylation reaction in an industrially advantageous manner, a technique of recycling the rhodium compound while maintaining its catalytic activity is required.

As a method for separating the reaction mixture into a rhodium catalyst and a product in the hydroformylation reaction, there is a method using distillation. Except the case where an aldehyde having a comparatively low boiling point is produced, the above method using distillation can hardly be regarded as advantageous from the viewpoint of the industrial practice, because the rhodium catalyst is deteriorated by the heat at the time of its separation by distillation. Particularly in the case where an aldehyde to be produced has a high boiling point, the condensation of the product tends to occur under the distillation conditions to form easily by-product of a higher-boiling point condensed material. Such a higher-boiling point condensed material is concentrated in a residual liquid in a still by distillation and is accumulated gradually with the recycling of the catalyst. This increases the viscosity of the residual liquid in the still, so that, even if the catalytic activity of the catalyst is maintained, the operability of the reaction is lost with the proceeding of the production of the aldehyde, which actually prevents the recycling of the catalyst. Furthermore, owing to heat, cross-linking reaction of this higher-boiling point condensed material happens to occur, which solidifies the residual liquid in the still and makes it impossible to carry out recycling of the catalyst.

Owing to such a problem in the operability, it is inevitable to renew the catalyst in a short time in the case of separating the rhodium catalyst from the product by distillation, except the case where an aldehyde having a relatively low boiling point is produced.

As a process for avoiding the above-described problem involved by the separation of the catalyst from the product by distillation, Japanese Patent Application Laid-Open No. SHO 58-157739 provides a process in which, using a water-soluble rhodium catalyst, a hydroformylation reaction is effected in the aqueous solvent and then the product is separated by extraction using an extractant such as a hydrocarbon. In addition, U.S. Pat. No. 5,180,854 discloses a process in which a hydroformylation reaction is effected, with the water-soluble rhodium catalyst dissolved in a reaction mixture using a solubilizing agent such as N-methylpyrrolidone, and then the catalyst is separated by extraction using water as an extractant.

The process disclosed in Japanese Patent Application Laid-Open No. SHO 58-157739 for the separation of the product by extraction is excellent in that (1) the catalyst is free from the heat and deactivation and (2) accumulation of the high-boiling point condensed material is avoided. But, the process is not advantageous for the industrial application, because it requires a large amount of a solvent and therefore a large-scaled reaction apparatus, which lowers a volumetric efficiency of the reaction, and moreover a great amount of energy upon the recovery of the extractant from the extract.

On the other hand, the process disclosed in U.S. Pat. No. 5,180,854 for the extraction of the catalyst is excellent in that i) the catalyst is free from thermal deterioration, ii) accumulation of a high-boiling point condensed material is avoided and iii) a high volumetric efficiency is achieved.

The present inventors carried out the hydroformylation reaction of an olefinic compound in accordance with the process disclosed in the above U.S. patent in view of the above advantages i)–iii). It has been recognized that the process is accompanied with the following problems. Described specifically, while recycling of a catalyst is repeated, selectivity to the byproduct which has a higher boiling point than the target aldehyde increases with the proceeding of the production of the aldehyde. This means that the selectivity to the target aldehyde decreases with the proceeding of the production of the aldehyde. Such a byproduct has an influence of the reduction of the recovery ratio of the catalyst or extends the time necessary for the separation of the water layer containing the catalyst. In addition, together with the lowering in the selectivity to the target aldehyde, the lowering in the catalytic activity has also been recognized.

Such problems appear notably in the case where a compound having at least two aldehyde groups is obtained by carrying out hydroformylation reaction of an olefinic compound having a formyl group, such as 7-octen-1-al, or of an olefinic compound having at least two ethylenic double bonds to which a formyl group is introduced by the hydroformylation reaction, such as 1,7-octadiene. For example, upon hydroformylation of 7-octen-1-al, the selectivity to the high-boiling point condensed material which is a byproduct finally becomes 10% or higher based on 7-octen-1-al.

In this way, even in the process described in U.S. Pat. No. 5,180,854, there exist some problems to be solved in order to carry out the hydroformylation reaction of an olefinic compound industrially advantageously.

So, an object of the present invention is therefore to provide an industrially advantageous process for the production of an aldehyde by the hydroformylation of an olefinic compound using a rhodium catalyst, by overcoming the problems such as thermal deterioration of the catalyst, limitation in the recycling of the catalyst owing to the accumulation of a high-boiling point condensed material, lowering in the volumetric efficiency of the reaction caused by the use of a large volume of a solvent, an increase in the selectivity to the high-boiling point byproduct with the proceeding of the production of the aldehyde and the lowering in the catalytic activity.

DISCLOSURE OF THE INVENTION

The present inventors have conducted an extensive research with a view to overcome the above-described problems. As a result, the present inventors have completed the present invention based on the finding that the increase in the selectivity to the high-boiling point byproduct with the proceeding of the production of an aldehyde and lowering in the catalytic activity can be prevented by adding an acidic substance to a catalytic component which has been separated from the hydroformylated product of an olefinic compound by the extraction using water as an extractant and recycling the resulting mixture for the hydroformylation reaction of the olefinic compound.

In one aspect of the present invention, there is provided a process for the hydroformylation of an olefinic compound, which comprises, upon the reaction of an olefinic compound with hydrogen and carbon monoxide, carrying out the reaction in the presence of:
a) a rhodium compound,
b) a tertiary organic phosphorus compound represented by the following formula (1):

$$P(X_1)(X_2)(X_3-SO_3M) \qquad (1)$$

wherein $X_1$ and $X_2$ each independently represents a monovalent hydrocarbon group having 1–15 carbon atoms, $X_3$ represents a divalent hydrocarbon group having 1–15 carbon atoms and M represents an alkali metal, and
c) a polar organic compound; separating the rhodium compound, the tertiary organic phosphorus compound represented by the formula (1) and the polar organic compound from the resulting reaction mixture by extraction with water; subjecting the extracted water layer to removal of water and addition of at least one acidic substance selected from sulfonic acids to prepare a concentrate containing the rhodium compound, the tertiary organic phosphorus compound represented by the formula (1) and the polar organic compound; and recycling the resulting concentrate to a reactor for reuse.

In another aspect of the present invention, there is also provided a process for the preparation of a hydroformylated product of an olefinic compound, which comprises, upon the reaction of an olefinic compound with hydrogen and carbon monoxide, carrying out the reaction in the presence of:
a) a rhodium compound,
b) a tertiary organic phosphorus compound represented by the above formula (1), and
c) a polar organic compound; separating the rhodium compound, the tertiary organic phosphorus compound represented by the formula (1) and the polar organic compound from the resulting reaction mixture by extraction with water; subjecting the extracted water layer to removal of water and addition of at least one acidic substance selected from sulfonic acids to prepare a concentrate containing the rhodium compound, the tertiary organic phosphorus compound represented by the formula (1) and the polar organic compound; and recycling the resulting concentrate to a reactor for reuse.

BEST MODE FOR WORKING THE INVENTION

The present invention will be described in detail.

In the hydroformylation process of the present invention, an olefinic compound to be hydroformylated is a compound which has an ethylenic carbon-carbon double bond and permits the formation of a corresponding aldehyde by the reaction with hydrogen and carbon monoxide. Such an olefinic compound can contain a substituent which does not inhibit the hydroformylation reaction. Examples of such a substituent include formyl group; hydroxyl group; alkoxy groups such as methoxy and ethoxy; alkoxycarbonyl groups such as methoxycarbonyl, ethoxycarbonyl and t-butoxycarbonyl; cyano group; and halogen atoms such as chlorine and bromine.

Specific examples of the olefinic compound include unsaturated hydrocarbons such as 1-butene, 2-butene, isobutene, 1-hexene, 1-octene, cyclohexene, styrene, 1,5-hexadiene, 1,7-octadiene, vinylcyclohexene, dicyclopentadiene and cyclooctadiene; unsaturated aldehydes such as 7-octen-1-al; unsaturated alcohols such as 7-octen-1-ol and 2,7-octadien-1-ol; acrylonitrile, vinyl acetate, vinyl chloride and methyl methacrylate.

The hydroformylation process of the present invention is particularly useful in the case where a compound having at least two aldehyde groups is prepared using as a starting material an ethylenic compound having a formyl group or an ethylenic compound which has at least two ethylenic double bonds to which a formyl group is introduced, for example, 1,5-hexadiene, 1,7-octadiene, vinylcyclohexene, dicyclopentadiene, cyclooctadiene, 7-octen-1-al or 2,7-octadien-1-ol.

As the rhodium compound usable in the present invention, a rhodium compound which has catalytic activity for hydroformylation or which can be converted to a compound with a catalytic activity for hydroformylation under the hydroformylation reaction conditions can be employed. Examples of such rhodium compound include $Rh_4(CO)_{12}$, $Rh_6(CO)_{16}$, $Rh(acac)(CO)_2$, rhodium oxide, rhodium chloride, rhodium acetylacetonate and rhodium acetate. The rhodium compound is generally used so that its concentration falls within a range of from 0.005 milligram atom to 5 milligram atom in terms of a rhodium atom per liter of the hydroformylation reaction mixture.

A description will next be made of the tertiary organic phosphorus compound represented by the formula (1) which is usable in the present invention.

Examples of the monovalent hydrocarbon group having 1–15 carbon atoms represented by $X_1$ or $X_2$ in the above-described formula (1) of the tertiary organic phosphorus compound include alkyl groups such as n-butyl and octyl; aryl groups such as phenyl, tolyl and naphthyl; cycloalkyl groups such as cyclohexyl and aralkyl groups such as benzyl. Examples of the divalent hydrocarbon group having 1–15 carbon atoms represented by $X_3$ include 1,3-phenylene group and tetramethylene group. Examples of the alkali metal represented by M include lithium, sodium and potassium.

Specific examples of the tertiary organic phosphorus compound represented by the formula (1) include sodium 3-diphenylphosphino-1-benzenesulfonate ($x_1=x_2$=phenyl group, $X_3$=1,3-phenylene group, M=sodium), lithium 3-diphenylphosphino-1-benzenesulfonate ($X_1=X_2$=phenyl group, $X_3$=1,3-phenylene group, M=lithium), sodium 3-butylphenylphosphino-1-benzenesulfonate ($X_1$=n-butyl group, $X_2$=phenyl group, $X_3$=1,3-phenylene group, M=sodium), sodium 3-butylcyclohexylphosphino-1-benzenesulfonate ($X_1$=n-butyl group, $X_2$=cyclohexyl group, $X_3$=1,3-phenylene group, M=sodium), sodium 3-bis(1-methylethyl)phosphino-1-benzenesulfonate ($X_1=X_2$=1-methylethyl group, $X_3$=1,3-phenylene group, M=sodium), lithium 3-dicyclohexylphosphino-1-benzenesulfonate ($X_1=X_2$=cyclohexyl group, $X_3$=1,3-phenylene group, M=lithium), sodium 3-dicyclohexylphosphino-1-benzenesulfonate ($X_1=X_2$=cyclohexyl group, $X_3$=1,3-phenylene group, M=sodium), potassium 3-dicyclohexylphosphino-1-benzenesulfonate ($X_1=X_2$=cyclohexyl group, $X_3$=1,3-phenylene group, M=potassium), sodium 3-hexadecylphenylphosphino-1-benzenesulfonate ($X_1$=n-hexadecyl group, $X_2$=phenyl group, $X_3$=1,3-phenylene group, M=sodium), sodium 3-dicyclohexylphosphino-1-propanesulfonate ($X_1=X_2$=cyclohexyl group, $X_3$=trimethylene group, M=sodium), sodium 3-diphenylphosphino-1-propanesulfonate ($X_1=X_2=$ phenyl group, $X_3=$trimethylene group, M=sodium), sodium 4-diphenyl-phosphino-1-butanesulfonate ($X_1=X_2=$phenyl group, $X_3=$tetramethylene group, M=sodium), sodium 4-(1, 1-dimethylethyl)-(phenyl)phosphino-1-butanesulfonate ($X_1=$t-butyl group, $X_2=$phenyl group, $X_3=$tetramethylene group, M=sodium), sodium 3-diethylphosphino-1-propanesulfonate ($X_1=X_2=$ethyl group, $X_3=$trimethylene group, M=sodium) and sodium 3-dihexylphosphino-1-propanesulfonate ($X_1=X_2=$n-hexyl group, $X_3=$trimethylene group, M=sodium).

The tertiary organic phosphorus compounds represented by the formula (1) is a water-soluble phosphine ligand.

The tertiary organic phosphorus compounds represented by the formula (1) can be used singly or at least two of them can be used in combination.

The tertiary organic phosphorus compound represented by the formula (1) is used in an amount within a range of at least 1 mmol, preferably at least 2 mmol, more preferably at least 5 mmol per liter of the hydroformylated reaction mixture, from the viewpoints of the selectivity to the hydroformylated product and thermal stability of the catalyst upon removal of water from the rhodium-compound-containing water layer obtained by the extraction described later. At the same time, it is desired to adjust its amount to be at least 20 moles relative to 1 gram atom of rhodium. Although no particular limitation is imposed on the upper limit of the amount of the tertiary organic phosphorus compound represented by the formula (1), it is desired to adjust its concentration to an extent not causing precipitation of insoluble matters in the stage of removing water from the catalyst-containing water layer. In consideration of the manufacturing cost or the like, it is desired to control the concentration of the tertiary organic phosphorous compound represented by the formula (1) to be 200 mmol or smaller per liter of the hydroformylated reaction mixture.

The polar organic compound used in the present invention is a compound which is inert to the hydroformylation reaction of an olefinic compound and also inert to the olefinic compound and its hydroformylated product; which can be mixed homogeneously with the olefinic compound and the reaction product, and separate into two layers, that is, a water layer and an organic layer, when the reaction mixture containing said polar organic compound is mixed with water; and at least one portion of which can be extracted in the water layer from the reaction mixture. The polar organic compound can preferably be mixed homogeneously with the tertiary organic phosphorus compound represented by the formula (1).

Examples of such a polar organic compound include sulfoxides such as dimethyl sulfoxide, sulfones such as sulfolane, carbonates such as ethylene carbonate, amides such as N-methylpyrrolidone and N,N-dimethylformamide, nitrites such as acetonitrile, diols such as ethylene glycol and butanediol, polyalkylene glycols such as diethylene glycol or polyethylene glycol (number-average molecular weight: 400), polyalkylene glycol monomethyl ethers such as polyethylene glycol monomethyl ether (number average molecular weight: 400), and polyalkylene glycol dimethyl ethers such as triethylene glycol dimethyl ether, tetraethylene glycol dimethyl ether and polyethylene glycol dimethyl ether (number average molecular weight: 400). Among them, dimethyl sulfoxide, N-methylpyrrolidone, N,N-dimethylformamide, polyethylene glycol having a number average molecular weight of not smaller than 300 but not larger than 600 and polyethylene glycol dimethyl ether having a number average molecular weight of not smaller than 300 but not larger than 600 are preferred from the viewpoints of its extraction recovery ratio into the water layer and separability from water after extraction. In addition, they are comparatively easily available so that they are preferable polar organic compounds for the industrial practice of the process of the present invention.

These polar organic compounds can be used singly or at least two of these compounds can be used as a mixture.

The polar organic compound is generally used so that its concentration in the hydroformylated reaction mixture falls within a range of not lower than 2 vol. % but not higher than 30 vol. %, preferably within a range of not lower than 5 vol. % but not higher than 20 vol. %.

The hydroformylation reaction is generally conducted at the temperature within a range of 40°–140° C., preferably 70°–120° C. The molar ratio of hydrogen to carbon monoxide used for the reaction generally falls within a range of from 1:2 to 5:1 as an inlet gaseous ratio. The reaction pressure generally falls within a range of from normal pressure to 300 atmospheric pressure, preferably within a range of 2–100 atomospheric pressure.

The hydroformylation reaction can be effected in a continuous manner or batch-wise manner in a known reaction apparatus such as stirring-type reaction vessel or bubble-column type reaction vessel.

The reaction mixture obtained by the above-described hydroformylation reaction is subjected to extraction with water, so that a catalyst component composed of the rhodium compound and the tertiary organic phosphorus compound represented by the formula (1), and the polar organic compound may be separated. It is preferred that the volume ratio of water relative to the reaction mixture falls within a range of not lower than $\frac{1}{20}$ but not higher than $\frac{2}{1}$, preferably within a range of not lower than $\frac{1}{20}$ but not higher than $\frac{1}{1}$.

The extraction temperature generally falls within a range of 10°–90° C. The extraction is generally carried out in an atmosphere of an inert gas such as nitrogen, helium or argon or a gaseous mixture of hydrogen and carbon monoxide.

The separability of the organic layer from the water layer in the above extraction depends on the polarities of the olefinic compound (starting material) and the resulting aldehyde, extraction temperature, the content of the polar organic compound in the reaction mixture or the like. In general, the higher the extraction temperature becomes or the higher the concentration of the polar organic compound becomes, the separability tends to be improved.

By such an extraction, the olefinic compound (starting material) and hydroformylated product are separated into the organic layer (the remaining layer after extraction), while the rhodium compound and the tertiary organic phosphorus compound represented by the formula (1) (which may hereinafter be called "catalytic component" collectively) and the polar organic compound are transferred to the water layer (extract layer). The organic layer contains small amounts of the catalytic component and polar organic compound in addition to the starting material and hydroformylated product. Accordingly, it is advantageous, from the viewpoint of industrially carrying out the process of the present invention, to subject again the resulting organic layer to extraction with water in order to make the recovery ratio of the catalytic component and the polar organic compound higher. In this case, no upper limit is imposed on the amount of water, but water is generally used at a volume ratio of not higher than an equivalent volume relative to that of the organic layer.

Even if the recovery ratio of the catalytic component and the polar organic compound is thus optimized, their loss sometimes reaches the level which cannot be neglected. In such a case, the catalytic component and polar organic compound may be added newly as needed.

The water layer containing the catalytic component and polar organic compound obtained by the above extraction is concentrated by the removal of water. For the removal of water, a known method can be applied without particular limitation. Among the known method, evaporation under reduced pressure is convenient. In this case, in order to avoid the deactivation of the catalyst such as thermal deterioration, it is desired to remove water at a temperature as low as possible. The temperature generally falls within a range of from 30° C. to 100° C. The pressure at the evaporation is generally within a range of from 300 mmHg to 10 mmHg.

It is necessary to remove water until the separation of the reaction mixture into an organic layer and a water layer is not observed when the resulting concentrate obtained is recycled to the hydroformylation reaction of an olefinic compound.

In the present invention, the separation of the reaction mixture into an organic layer and a water layer can be avoided by decreasing the content of water in the concentrate when the concentrate is recycled to the hydroformylation reaction of an olefinic compound. It is, however, preferred not to carry out the removal of water excessively, because an extreme reduction in the water content in the concentrate requires a great amount of heat, which increases a manufacturing cost and also increases an amount of heat applied to the catalyst to cause thermal deterioration of the catalyst.

The water layer containing the catalytic component and the polar organic compound obtained by the above-described extraction, and the concentrate obtained by removing water from the water layer are generally a little alkaline. In the present invention, at least one acidic substance selected from sulfonic acids is added to the water layer or the concentrate to adjust it to the neutral side.

Specific examples of the acidic substance selected from sulfonic acids include benzenesulfonic acid, toluenesulfonic acid and 3-diphenylphosphino-1-benzenesulfonic acid. Among them, a phosphorus-containing sulfonic acid represented by the following formula (2):

$$P(X_4)(X_5)(X_6-SO_3H) \qquad (2)$$

wherein $X_4$ and $X_5$ each independently represents a monovalent hydrocarbon group having 1–15 carbon atoms and $X_6$ represents a divalent hydrocarbon group having 1–15 carbon atoms, such as 3-diphenylphosphino-1-benzenesulfonic acid, is preferred.

Examples of the monovalent hydrocarbon group having 1–15 carbon atoms represented by $X_4$ or $X_5$ include alkyl groups such as n-butyl and octyl; aryl groups such as phenyl, tolyl and naphthyl; cycloalkyl groups such as cyclohexyl and aralkyl groups such as benzyl. Examples of the divalent hydrocarbon group having 1–15 carbon atoms represented by $X_6$ include 1,3-phenylene group and tetramethylene group.

Specific examples of the phosphorus-containing sulfonic acid represented by the formula (2) include 3-diphenylphospino-1-benzenesulfonic acid ($X_4=X_5=$ phenyl group, $X_6=1,3$-phenylene group), 3-butylphenylphosphino-1-benzenesulfonic acid ($X_4=$n-butyl group, $X_5=$phenyl group, $X_6=1,3$-phenylene group), 3-butylcyclohexylphosphino-1-benzenesulfonic acid ($X_4=$n-butyl group, $X_5=$cyclohexyl group, $X_6=1,3$-phenylene group), 3-bis(1-methylethyl)phosphino-1-benzenesulfonic acid ($X_4=X_5=$1-methylethyl group, $X_6=1,3$-phenylene group), 3-dicyclohexylphosphino-1-benzenesulfonic acid ($X_4=X_5=$cyclohexyl group, $X_6=1,3$-phenylene group), 3-hexadecylphenylphosphino-1-benzenesulfonic acid ($X_4=$n-hexadecyl group, $X_5=$phenyl group, $X_6=1,3$-phenylene group), 3-dicyclohexylphosphino-1-propanesulfonic acid ($X_4=X_5=$cyclohexyl group, $X_6=$trimethylene group), 3-diphenylphosphino-1-propanesulfonic acid ($X_1=X_5=$ phenyl group, $X_6=$trimethylene group), 4-diphenylphosphino-1-butanesulfonic acid ($X_4=X_5=$phenyl group, $X_5=$tetramethylene group), 4-(1,1-dimethylethyl)(phenyl)phosphino-1-butanesulfonic acid ($X_4=$t-butyl group, $X_6=$phenyl group, $X_6=$tetramethylene group), 3-diethylphosphino-1-propanesulfonic acid ($X_4=X_5=$ethyl group, $X_6=$trimethylene group) and 3-dihexylphosphino-1-propanesulfonic acid ($X_4=X_5=$n-hexyl group, $X_5=$trimethylene group).

Such an acidic substance can be added as it is or as a solution dissolved in water or a polar organic compound.

By the addition of an acidic substance, the amount of a basic substance in the water layer or concentrate decreases.

The amount of the acidic substance is determined depending on the amount of a basic substance. Described specifically, it is determined after the amount of the basic substance in the above water layer or concentrate is measured by a pH-meter or in a known method such as titration. Since the amount of the basic substance differs with the kind and amount of the olefinic compound which is a starting material, conditions of hydroformylation reaction, the kind of rhodium compound, the kinds and amounts of the tertiary organic phosphorus compound represented by the formula (1) and the polar organic compound or extraction conditions with water, the amount of the acidic substance cannot be specified in a wholesale manner. It is, however, preferred to add the acidic substance in an amount so that the water layer or concentrate can be adjusted to almost neutral.

The acidic substance can be added in an amount exceeding the amount necessary for the neutralization of the basic substance. But the addition of too excess amount of the acidic substance causes not only corrosion of the reaction apparatus but also reduction in the reaction rate. Therefore, it is not preferred to add the acidic substance excessively. The upper limit of the amount of the acidic substance is set so that the acidic substance may exist preferably in the concentrate in an amount of about 3 mmol per liter of the concentrate, more preferably in an amount of about 1 mmol per liter of the concentrate.

The acidic substance is generally added after water is removed from the water layer, but it is also possible to add the acidic substance prior to the water removal. In this case, water is removed after the addition of the acidic substance.

The acidic substance can be added either continuously or discontinuously at appropriate intervals.

Incidentally, treatment with a strong-acid-type ion exchange resin such as a sulfonic acid type resin, instead of the addition of the acidic substance, can reduce the amount of the basic substance in the water layer or the concentrate and achieve the similar effects as above.

It is advantageous, from the viewpoint of industrially carrying out the process of the present invention, to, after the addition of acidic substance as above, recycle the concentrate, which contains the rhodium compound, the tertiary organic phosphorus compound represented by the formula (1) and the polar organic compound, to the hydroformylation reaction of an olefinic compound while maintaining its temperature within a range of 30°–80° C. to avoid the thermal deterioration of the rhodium compound.

From the organic layer after the extraction of the catalytic component, an aldehyde can be obtained as a product in a known method such as distillation or crystallization. Alternatively, the organic layer containing the aldehyde can be used, as it is, as a starting material for the reaction such as oxidation or hydrogenation.

Any one of the above-described operations such as hydroformylation reaction, separation of the catalytic component by the extraction with water, removal of water from the water layer and the addition of an acidic substance can be carried out in a batch-wise manner or continuous manner.

The present invention will hereinafter be described more specifically by examples. It should, however, be borne in mind that the present invention will not be limited to or by the following examples.

EXAMPLE 1

The hydroformylation reaction of 7-octen-1-al was carried out in a continuous manner by using the reaction apparatus, extraction apparatus and a thin-film evaporation apparatus described subsequently.

Reaction apparatus

A stainless-made autoclave which is equipped a starting material feed pump, a catalyst liquid feed pump, a supplemental catalyst liquid feed pump, a pressure regulator for feeding of a gaseous mixture of carbon monoxide and hydrogen, a reaction mixture feed pump, a temperature controller, an electromagnetic stirrer with four baffles and an off-gas purge port.

The starting material, 7-octen-1-al, is fed into the autoclave through the starting material feed pump, while the gaseous mixture of carbon monoxide and hydrogen is introduced into the autoclave through the pressure regulator for feeding of the gaseous mixture of carbon monoxide and hydrogen and is then discharged from the reaction system through the off-gas purge port.

The concentrate containing a catalytic component and a polar organic compound which is obtained by the extraction and concentration is fed through the catalyst liquid feed pump, and the supplemental portions of the catalytic component and polar organic compound are fed through the supplemental catalyst liquid feed pump, respectively to the autoclave. The reaction mixture is then fed to the extraction apparatus through the reaction mixture feed pump.

Extraction apparatus

A mixer settler type extractor equipped with a water feed pump, a temperature controller, an organic layer feed pump, a water layer feed pump, an stirrer and a peeping glass.

The organic layer (the remaining layer after extraction) is fed through the organic layer feed pump to a storage tank having an internal volume of 20 liters. The water layer (extract layer) is fed through the water layer pump to the thin-film evaporation apparatus.

Thin-film evaporation apparatus

A thin-film evaporation apparatus equipped with a vacuum pump, a pressure controller, a cooler, a temperature controller and a concentrate receiver.

The concentrate obtained is fed from the concentrate receiver to the reaction apparatus (autoclave) through the catalyst liquid feed pump.

The olefinic compound, rhodium compound, tertiary organic phosphorus compound represented by the formula (1) and polar organic compound employed are as follows:

Olefinic compound: 7-octen-1-al (containing 10 vol. % of 1-octanal)

Rhodium compound: rhodium dicarbonyl acetylacetonate [Rh(acac) (CO)$_2$]

Tertiary organic phosphorus compound represented by the formula (1):

Sodium 3-diphenylphosphino-1-benzenesulfonate which will hereinafter be abbreviated as "TPPS-Na")

Polar organic compound: polyethylene glycol dimethyl ether having a number average molecular weight of 400.

The operation conditions in a stationary state are as follows:

1. Hydroformylation reaction

Reaction temperature: 80° C.

Reaction pressure: 30 kg/cm$^2$G (gauge pressure) (partial pressure ratio of carbon monoxide to hydrogen=1:1)

Off-gas rate: 20 liters/h

Volume of liquid to be reacted: 380 ml

Feeding rate of starting materials: 20 ml/h

Here, the feeding rates of the catalytic component and polar organic compound, as a sum of those recovered by extraction and supplemented, are as follows:

Rhodium compound: 0.0022 mmol/h (of it, that supplemented: 0.0004 mmol/h)

Tertiary organic phosphorus compound represented by the formula (1): 0.11 mmol/h (of it, that supplemented: 0.03 mmol/h)

Polar organic compound: 2 ml/h (of it, that supplemented: 0.4 ml/h)

2. Extraction of the catalyst

Temperature inside the mixer settler: 50° C.

Feeding rate of water: 7 ml/h

Volume of liquid in the mixer settler: 300 ml

3. Water evaporation by a thin-film evaporator

Temperature: 90° C.

Pressure: 70 mnHg

Volume of concentrate: 50 ml

Here, the water content in the concentrate obtained by water evaporation was maintained at 10 wt. % or lower. The concentrate was fed to the hydroformylation reaction at a rate of about 1.7 ml/h.

An analysis of the organic layer (the remaining layer after extraction) in a stationary state with gas chromatography shows that the conversion of 7-octen-1-al was 95% and the reaction products were 1,9-nonanedial, 2-methyl-1,8-octanedial and a higher-boiling point condensed material. The ratio of 1,9-nonanedial to 2-methyl-1,8-octanedial was 75:25.

At the time when 384 hours had passed in a stationary state, the concentrate obtained by water evaporation was sampled, followed by titration to determine the amount of the acidic substance necessary for the neutralization of the basic substance in the concentrate. As a result, it has been found that the amount of the acidic substance was 4 milligram equivalents per liter of the concentrate. Here, 50 mg of 3-diphenylphosphino-1-benzenesulfonic acid (which will hereinafter be abbreviated as "TPPS") were added to the concentrate and the hydrofolmylation reaction was continued. 20 mg of TPPS were thereafter added to the concentrate at the intervals of 24 hours.

The time for the reaction and the amount of the higher-boiling point condensed material in the organic layer (remaining layer after extraction) at that time are shown in Table 1.

TABLE 1

| Time for the operation in a stationary state (hr) | Amount of a higher-boiling point condensed material in the organic layer (wt. %) |
|---|---|
| 24 | 1 |
| 120 | 5 |
| 240 | 11 |
| 360 | 16 |
| 480 | 4 |

EXAMPLE 2

In Example 1, at the time when 240 hours had passed in a stationary state, the concentrate obtained by water evaporation was sampled, followed by titration to determine the amount of the TPPS necessary for the neutralization of the basic substance in the concentrate. As a result, it has been found that the amount of TPPS was 1.2 g per liter of the concentrate.

In an electromagnetic stirring type autoclave having an internal volume of 100 ml, a predetermined amount of TPPS, 5 ml of the concentrate which had been obtained by the evaporation of water at the time when 240 hours had passed in a stationary state in Example 1 and 20 ml of 7-octen-1-al (purity 90%, 0.12 mol, containing 10% of 1-octanal) were charged while avoiding their contact with air. The pressure in the autoclave was maintained at 30 kg/cm$^2$G (gauge pressure) with a gaseous mixture of hydrogen and carbon monoxide at a ratio of 1:1 (molar ratio). An off-gas was discharged at a rate of 10 liters/h and internal temperature was raised to 70° C. while stirring. The reaction was conducted for 4 hours under that condition. The internal temperature was then raised to 100° C. over one hour and the reaction was conducted for 5 hours under that condition. The reaction mixture obtained was analyzed by gas chromatography to determine the conversion of 7-octen-1-al and amount of higher-boiling point condensed material. Results are shown in Table 2.

TABLE 2

| Amount of TPPS added (mg) | Conversion of 7-octen-1-al (after 4 hours, mol %) | Amount of higher-boiling point condensed material [wt. % (Note), after completion of the reaction] |
|---|---|---|
| 0 | 36 | 21 |
| 6 | 41 | 2 |
| 9 | 26 | 2 |

(Note) The amount of a higher-boiling point condensed material in the hydroformylated reaction mixture

EXAMPLE 3

In electromagnetic stirring type autoclave equipped with a gas inlet and a sampling port and having an internal volume of 300 ml, 1.29 mg (0.005 mmol) of rhodium dicarbonyl acetylacetonate, 800 mg (2 mmol) of TPPS-Na, 10 ml of dimethyl sulfoxide and 90 ml of 7-octen-1-al (purity: 90%, 0.55 mol, containing 10% of 1-octanal) were charged avoiding their contact with air. The pressure inside of the autoclave was maintained at 30 kg/cm$^2$G (gauge pressure) with gaseous mixture of hydrogen and carbon monoxide at a ratio of 1:1 (molar ratio). An off-gas was discharged at a rate of 10 liters/h and the internal temperature was raised to 90° C. while stirring. The reaction was carried out for 4 hours under those conditions.

The reaction mixture was then fed into a three-necked flask, filled sufficiently with a gaseous mixture of hydrogen and carbon monoxide at a ratio of 1:1 (molar ratio) in advance and having an internal volume of 250 ml, avoiding its contact with air. While 20 ml of water were added and the internal temperature was maintained at 25° C., the reaction mixture was stirred for 10 minutes under the atmosphere of the gaseous mixture of the above composition. After the stirring was stopped, the reaction mixture was transferred to the separation tank filled with a gaseous mixture of hydrogen and carbon monoxide and then allowed to stand, which separated the reaction mixture into an organic layer (upper layer) and a water layer (lower layer). The water layer was transferred to a flask filled with nitrogen and having an internal volume of 200 ml, which was immersed in a water bath kept at 60° C. Water was distilled by the gradual reduction of the pressure to 15 mmHg. When the distillation of water was completed, the pressure was adjusted to normal one with a nitrogen while maintaining the temperature at 60° C.

To the concentrate obtained, 80 mg of TPPS-Na, 1.5 ml of dimethyl sulfoxide and 90 ml of 7-octen-1-al were added, followed by mixing under stirring. Then, the concentrate mixture was transferred again to the autoclave avoiding its contact with air, and hydroformylation reaction was carried out for four hours under the reaction conditions similar to those employed for the first reaction. The extraction, water evaporation, and addition of TPPS-Na, dimethyl sulfoxide and starting materials were also conducted under similar conditions with those employed for the first reaction.

In this manner, hydroformylation reaction was repeated and hydroformylation reaction of 7-octen-1-al was carried out 22 times in total. Here, concerning the organic layer (remaining layer after extraction) obtained by the separation of the water layer containing the catalytic component and the polar organic compound, analysis of the product was carried out with gas chromatography.

Incidentally, to the concentrate of the water layer obtained by the treatment of the 10-th reaction mixture, 0.31 mg of rhodium dicarbonyl acetylacetonate was added. In addition, the concentrate of the water layer obtained by the treatment of the 20-th reaction mixture was subjected to titration. As a result, it has been found that the amount of TPPS necessary for the neutralization of the concentrate was 2 g per liter of the concentrate. To the concentrate, 0.31 mg of rhodium dicarbonyl acetylacetonate and 20 mg of TPPS were added. Reaction times and amounts of 1,9-nonanedial, 2-methyl-1,8-octanedial and higher-boiling point condensed material are shown in Table 3.

TABLE 3

| | Amount (g) | | |
|---|---|---|---|
| Reaction times | 1,9-Nonanedial | 2-Methyl-1,8-octanedial | Higher-boiling point condensed material |
| 1 | 46 | 15 | 0 |
| 5 | 44 | 15 | 1 |
| 10 | 41 | 13 | 3 |
| 15 | 43 | 14 | 4 |
| 20 | 39 | 13 | 7 |
| 21 | 45 | 15 | 1 |
| 22 | 46 | 15 | 1 |

As is evident from Tables 1–3, it has been found that the amount of the higher-boiling point condensed material was suppressed by the addition of TPPS to the concentrate of the water layer obtained by the extraction of the hydroformylation reaction mixture with water.

EXAMPLE 4

In an electromagnetic stirring type autoclave equipped with a gas inlet and a sampling port and having an internal volume of 300 ml, 2.58 mg (0.01 mmol) of rhodium dicarbonyl acetylacetonate, 2.0 g (5 mmol) of TPPS-Na, 50 ml of N-methylpyrrolidone and 45 ml (0.287 mol) of 1-octene were charged avoiding their contact with air. The pressure inside of the autoclave was maintained at 30 kg/cm$^2$G (gauge pressure) with a gaseous mixture of hydrogen and carbon monoxide at a ratio of 1:1 (molar ratio). The internal temperature was raised to 90° C. under stirring, under which condition the reaction was effected for 3 hours. The internal temperature was raised further to 110° C., under which condition the reaction was conducted for 4 hours.

The reaction mixture was then fed into a three-necked flask, filled sufficiently with a gaseous mixture of hydrogen and carbon monoxide at a ratio of 1:1 (molar ratio) in advance and having an internal volume of 250 ml, avoiding its contact with air. While 20 ml of water were added and the internal temperature was maintained at 25° C., the reaction mixture was stirred for 10 minutes under the atmosphere of the gaseous mixture of the above composition. After stirring was stopped, the reaction mixture was transferred to the separation tank filled with a gaseous mixture of hydrogen and carbon monoxide and then allowed to stand, which separated the reaction mixture into two layers, that is, an organic layer (upper layer) and a water layer (lower layer). The water layer was transferred to a flask filled with nitrogen and having an internal volume of 200 ml, followed by immersion in a water bath kept at 60° C. Water was distilled by the gradual reduction of the pressure to 15 mmHg. When the distillation of water was completed, the pressure was adjusted to the normal one with a nitrogen while maintaining the temperature at 60° C.

To the concentrate obtained, 100 mg of TPPS-Na, 8.6 ml of N-methylpyrrolidone and 45 ml of 1-octene were added, followed by mixing under stirring. Then, the concentrate mixture was transferred again to the autoclave avoiding its contact with air, and hydroformylation reaction was carried out under the reaction conditions similar to those employed for the first reaction. The extraction, water evaporation, and addition of TPPS-Na, N-methylpyrrolidone and 1-octene were also conducted under similar conditions with those employed for the first reaction.

In this manner, hydroformylation reaction was repeated and hydroformylation reaction was carried out 17 times in total. Here, the organic layer obtained by the separation of the water layer containing the catalytic component and N-methylpyrrolidone was subjected to analysis of the product with gas chromatography. In addition, the amount of higher-boiling point condensed material in the organic layer was determined by the gas chromatographic analysis of the concentrate obtained from said organic layer by the gradual reduction of the pressure to 5 mmHg at 110° C., which is about 15-fold to 20-fold concentration relative to the original organic layer.

Incidentally, to each of the concentrate of the water layer obtained by the treatment of the 5-th, 10-th and 15-the reaction mixtures, respectively, 1.29 mg of rhodium dicarbonyl acetylacetonate was added. Analysis of the water layer obtained by the treatment of the 15-th reaction mixture with a pH-meter shows that the addition of 0.3 g of TPPS per liter of the concentrate changes the property of the concentrate from basic to acidic. To the concentrate, 12 mg of TPPS was added.

Reaction times and results of analysis of the organic layer obtained by the treatment of the reaction mixture are shown in Table 4.

TABLE 4

| | Amount (wt. %) | |
|---|---|---|
| Reaction times | Aldehyde having 9 carbon atoms (Note) | Higher-boiling point condensed material |
| 1 | 82 | 1.2 |
| 11 | 79 | 2.2 |
| 15 | 74 | 3.0 |
| 16 | 78 | 1.4 |
| 17 | 79 | 1.5 |

(Note) Mixture of 1-nonanal and 2-methyloctanal

As evident from Table 4, it has been found that the amount of the higher-boiling point condensed material can be suppressed by the addition of TPPS to the concentrate of the water layer obtained by the extraction of the hydroformylation reaction mixture with water.

INDUSTRIAL UTILIZATION

The hydroformylation process of the present invention is useful as an industrial preparation process of various aldehydes useful as a starting material for fine chemicals such as pharmaceuticals and agricultural chemicals, alcohols for a plasticizer or starting materials such as diol, dicarboxylic acid, and diamine for the synthesis of a polymer compound.

We claim:

1. A process for the hydroformylation of an olefinic compound, which comprises, upon the reaction of the olefinic compound with hydrogen and carbon monoxide, carrying out the reaction in the presence of:
   a) a rhodium compound
   b) a tertiary organic phosphorous compound represented by the following formula (1):

$$P(X_1)(X_2)(X_3\text{—}SO_3M) \tag{1}$$

wherein $X_1$ and $X_2$ each independently represents a monovalent hydrocarbon group having 1–15 carbon atoms, $X_3$ represents a divalent hydrocarbon group having 1–15 carbon atoms and M represents an alkali metal, and
   c) a polar organic compound; separating the rhodium compound, the tertiary organic phosphorous compound represented by the formula (1) and the polar organic compound from the resulting reaction mixture by extraction with water; subjecting the extracted water layer to removal of water and addition of at least one acidic substance selected from sulfonic acids in an amount to adjust the pH of the extracted water layer to at least about neutral to prepare a concentrate containing the rhodium compound, the tertiary organic phosphorous compound represented by the formula (1) and the polar organic compound; and recycling the resulting concentrate to a reactor for reuse.

2. The hydroformylation process of an olefinic compound according to claim 1, wherein the olefinic compound is an olefinic compound having a formyl group or an olefinic compound which has at least two ethylenic double bonds to which a formyl group is introduced by the hydroformylation reaction.

3. The hydroformylation process of an olefinic compound according to claim 1, wherein the polar organic compound is one or more than one compounds selected from the group consisting of dimethyl sulfoxide, sulfolane, ethylene carbonate, N-methylpyrrolidone, dimethylformamide, acetonitrile, ethylene glycol, butanediol, polyalkylene glycols, polyalkylene glycol monomethyl ethers and polyalkylene glycol dimethyl ethers.

4. The hydroformylation process of an olefinic compound according to claim 1, wherein the polar organic compound is a polyethylene glycol having a number average molecular weight of not lower than 300 but not higher than 600 and/or polyethylene glycol dimethyl ether having a number average molecular weight of not lower than 300 but not higher than 600.

5. The hydroformylation process of an olefinic compound according to claim 1, wherein the acidic substance is a phosphorus-containing sulfonic acid represented by the following formula (2):

$$P(X_4)(X_5)(X_6-SO_3H) \tag{2}$$

wherein $X_4$ and $X_5$ each independently represents a monovalent hydrocarbon group having 1–15 carbon atoms and $X_6$ represents a divalent hydrocarbon group having 1–15 carbon atoms.

6. A process for the preparation of a hydroformylated product of an olefinic compound, which comprises, upon the reaction of the olefinic compound with hydrogen and carbon monoxide, carrying out the reaction in the presence of:

a) a rhodium compound b) a tertiary organic phosphorous compound represented by the following formula (1):

$$P(X_1)(X_2)(X_3-SO_3M) \tag{1}$$

wherein $X_1$ and $X_2$ each independently represents a monovalent hydrocarbon group having 1–15 carbon atoms, $X_3$ represents a divalent hydrocarbon group having 1–15 carbon atoms and M represents an alkali metal, and c) a polar organic compound; separating the rhodium compound, the tertiary organic phosphorous compound represented by the formula (1) and the polar organic compound from the resulting reaction mixture by extraction with water; subjecting the extracted water layer to removal of water and addition of at least one acidic substance selected from sulfonic acids in an amount to adjust the pH of the extracted water layer to at least about neutral to prepare a concentrate containing the rhodium compound, the tertiary organic phosphorous compound represented by the formula (1) and the polar organic compound; and recycling the resulting concentrate to a reactor for reuse.

* * * * *